(12) United States Patent
Tommasi

(10) Patent No.: US 6,289,914 B1
(45) Date of Patent: Sep. 18, 2001

(54) MICROFLOW SPLITTER

(75) Inventor: Ruben A. Tommasi, Whitehouse Station, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/640,315

(22) Filed: Aug. 16, 2000

(51) Int. Cl.[7] .................................................. B07D 15/08
(52) U.S. Cl. .................. 137/15.18; 137/544; 137/561 A; 55/197
(58) Field of Search ............................ 137/561 A, 15.18, 137/544; 55/197

(56) References Cited

U.S. PATENT DOCUMENTS

| | | | | |
|---|---|---|---|---|
| 3,498,027 | * | 3/1970 | Buchtel | 55/197 |
| 3,590,866 | * | 7/1971 | Brownlee | 137/561 R |
| 3,640,822 | * | 2/1972 | Hrdina | 210/635 |
| 3,881,892 | * | 5/1975 | Gehrke et al. | 95/86 |
| 3,912,470 | * | 10/1975 | Fluckiger | 96/106 |
| 5,601,707 | * | 2/1997 | Clay et al. | 210/198.2 |

FOREIGN PATENT DOCUMENTS 0 495 255 A1   1/1991  (EP) .
2 343 673 A    10/1998 (GB) .

OTHER PUBLICATIONS

Journal of Chromatography B: Biomedical Applications, Aldo Roda, et al., 665(2), pp. 281–294 (1995).

Protein Science, Daniel Hess, et al., 2(8), pp. 1342–1351 (Aug. 1993).

Electrophoresis 2000, Michael D. McGinley, et al., 21(9), pp. 1678–1684.

Journal of Chromatography, Francois R. Sugnaux, et al., 264(3), pp. 357–376 (1983).

* cited by examiner

Primary Examiner—A. Michael Chambers
(74) Attorney, Agent, or Firm—Carol Loeschorn

(57) ABSTRACT

This invention refers to a microsplitter in flow systems especially used for separation techniques in analytical chemistry such as microliquid chromatography (MLC), high pressure liquid chromatography (HPLC) and ancillary techniques. The splitter system comprises a microsplitter and a micromixer which are connected by a microbore tubing. A high collection rate and high resolution of the sample peak are achieved by the proper choice of tubing length and diameters and the use of a back pressure regulator to obtain a controlled split ratio.

19 Claims, 3 Drawing Sheets

MICROFLOW SPLITTER

FIELD OF THE INVENTION

Figure 1:
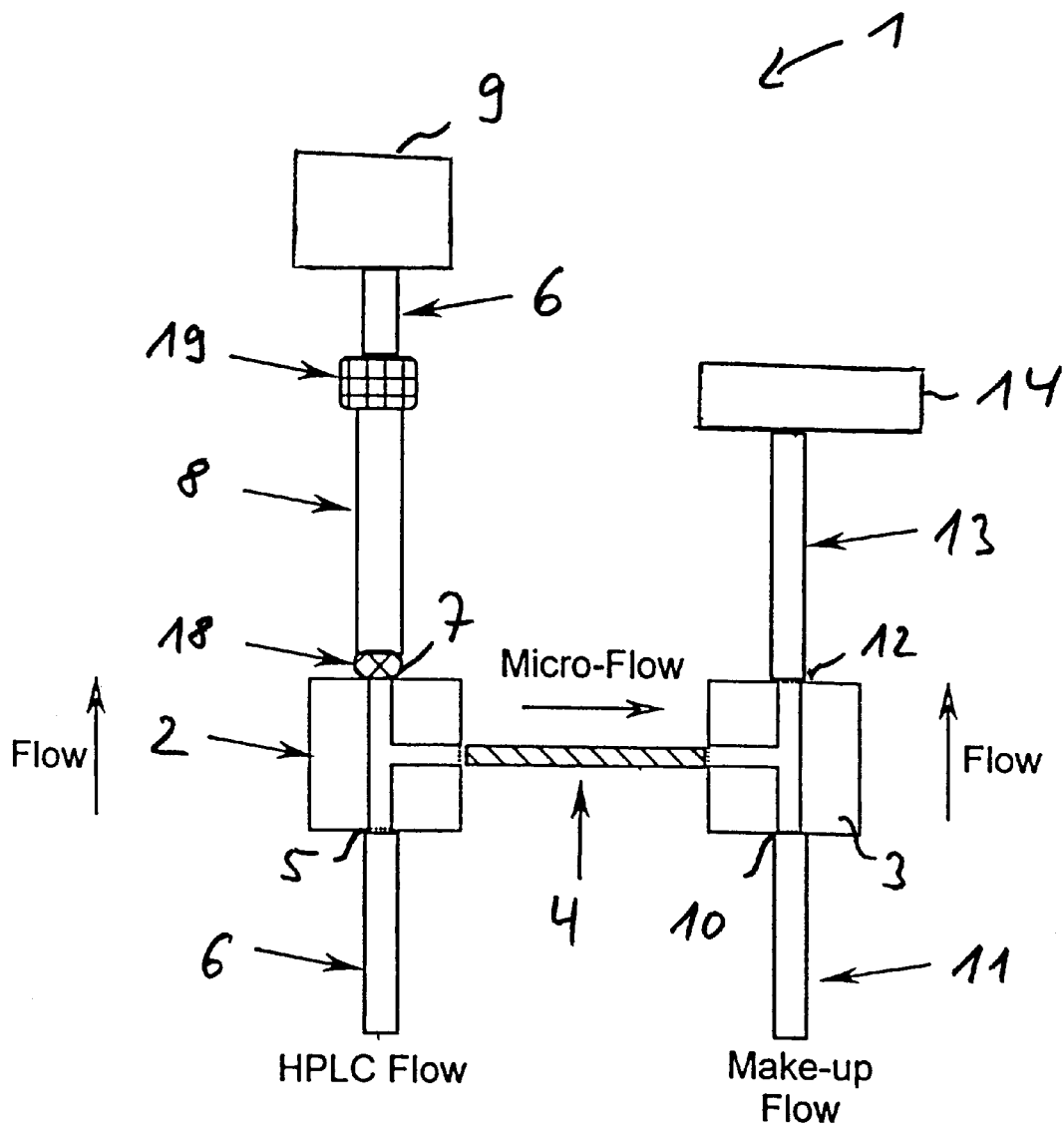

This invention refers to a microsplitter in flow systems especially used for separation techniques in analytical chemistry such as micro liquid chromatography (MLC), high-pressure liquid chromatography (HPLC) and ancillary techniques.

BACKGROUND OF THE INVENTION

Separation techniques such as MLC or HPLC are commonly used in analytical chemistry. These techniques offer high separation efficiency, high mass sensitivity and high resolution for the purification and separation of products of organic reactions. They are especially useful in pharmaceutical research for drug discovery. Normally, a UV cell or a light scattering cell is used for the detection of the sample. This cell is placed in line between the HPLC spectrometer and the fraction collector and is passed by the HPLC flow. However, for the identification of the substance a UV cell is not suitable. Therefore, a further detector such as a mass spectrometer is needed for the identification of the sample.

Certain detector systems require only a small amount of sample for detection and, therefore, cannot handle the relatively large sample volumes generated on a preparative scale. These detector systems require a split in the flow to divert the sample from the detector. For methods that are destructive to the sample, such as mass spectrometry and light scattering, a split in the flow is required in order to divert most of the sample to a fraction collector so that the desired materials can be collected.

Flow splitters are already known. In EP 495 255 A1 a flow splitter consisting of a micromixer and a microsplitter is described. However, the functionality that is currently available results in large broadening of the sample peaks and therefore loss of efficiency and potentially remixing of samples that would otherwise be collected in pure form.

The present invention is concerned with the problem of providing a microflow splitter system with a higher collection rate, minimized sample loss and higher resolution of the sample peak.

The invention solves this problem by providing a microflow splitter device consisting of a splitter system including a microsplitter and a micromixer which are connected by a microbore tubing. A high collection rate and high resolution of the sample peak are achieved by the proper choice of tubing length and diameters and the use of a back pressure regulator to obtain a controlled split ratio. More specifically, the present invention provides a microflow splitter device for the conversion of conventional flow rates (ml/min) into microflow rates ($\mu$l/min) in microseparation techniques, particularly for the collection of HPLC sample fractions which are detected and identified by a mass spectrometer, comprising a microsplitter (2) and a micromixer (3), which are connected by a microbore tubing (4), wherein said micromixer (3) is placed after said microsplitter (2) and wherein the microsplitter (2) is connected with a wide bore tubing (8) for the flow towards the fraction collector (9) which is equipped with a back pressure regulator (19) and a filter frit (18).

In a further embodiment, the present invention is directed to a process of making a microflow splitter device for the conversion of conventional flow rates (ml/min) into microflow rates ($\mu$l/min) in microseparation techniques, particularly HPLC techniques in connection with a mass spectrometer for identifying the samples, comprising the steps of:
  placing a micromixer behind a microsplitter;
  connecting said microsplitter to said micromixer by means of a microbore tubing;
  connecting a wide bore tubing for the flow towards the fraction collector with the microsplitter;
  inserting a back pressure regulator into said wide bore tubing; and inserting a filter frit into said wide bore tubing.

Figure 2:
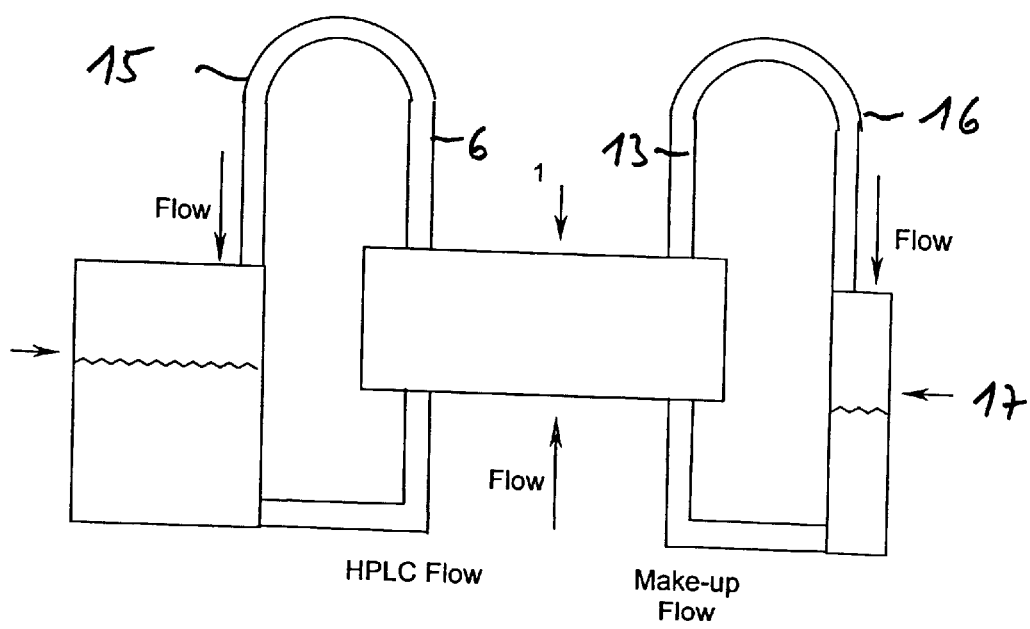
Figure 3:
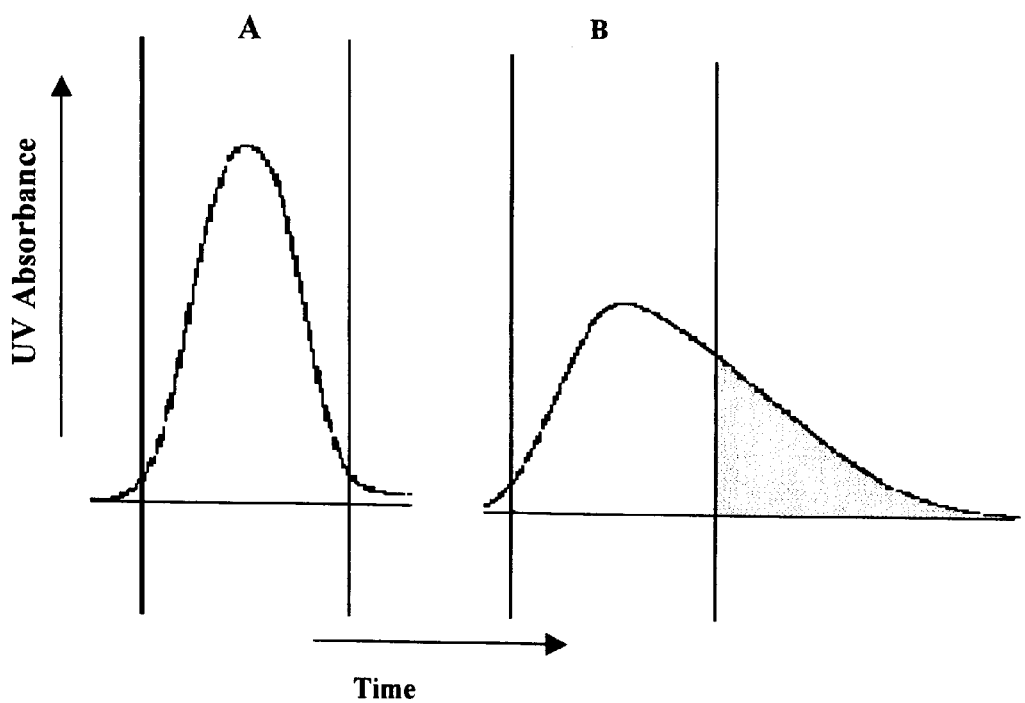
Figure 4:
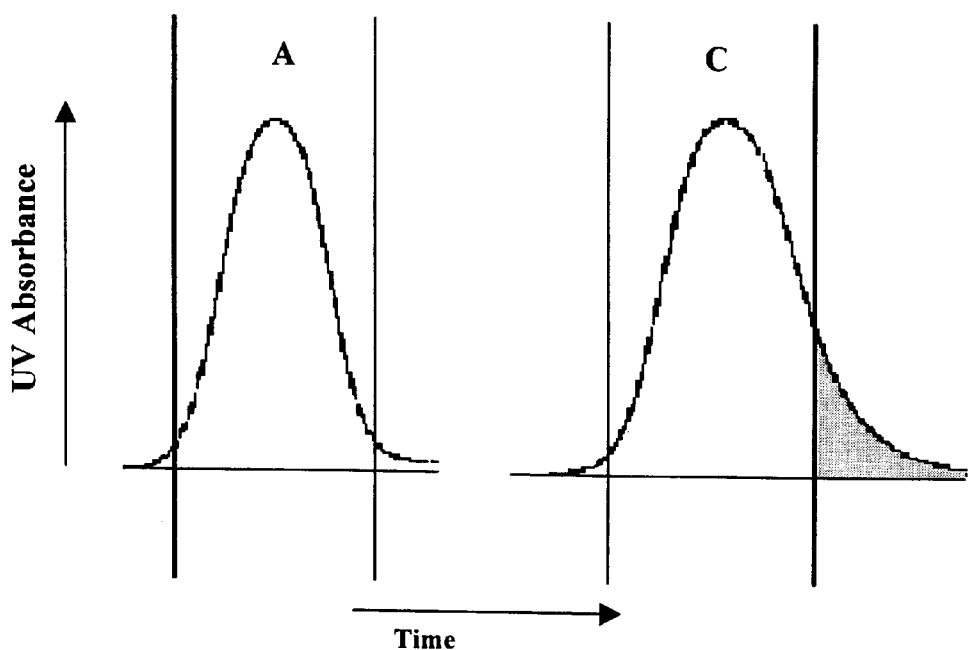

Further embodiments and advantages of the invention may be seen from the description that follows and the drawings. In the drawings, FIG. 1 shows a schematic illustration of an embodiment of a microflow splitter device according to the invention, FIG. 2 shows a setup for measuring the microflow split ratios, FIG. 3 shows a comparison of an HPLC trace with no splitter (A) and with a commercial splitter (B), FIG. 4 shows a comparison of an HPLC trace with no splitter (A) and with a splitter (B) according to the invention.

DETAILED DESCRIPTION OF THE INVENTION

A scheme of a microflow splitter device 1 is shown in FIG. 1. It consists of a microsplitter 2 and a micromixer 3 which are connected by a microbore tubing 4 and preferably mounted in a protective box. Advantageously, the microbore tubing 4 is a fused silica tubing typically 10–25 $\mu$m in radius, and having a length of 2–10 cm. The microsplitter 2 consists of a T-fitting with a port 5 which preferably is connected to a HPLC tubing 6 for the HPLC flow and a port 7 for the flow running through a tubing 8 to a fraction collector 9. The micromixer 3 consists as well of a T-fitting with a port 10 for a tubing 11 for a make-up flow and a second port 12 for a tubing 13 connected to a detector 14, e.g. a mass spectrometer. The connections can be made with any type of fitting that withstands high pressures and provides sufficient chemical stability, e.g. poly ether ether Ketone (PEEK) or stainless steel.

The HPLC flow coming from the HPLC enters the microsplitter 2 and is split by the T-fitting into a flow $F_1$ towards the fraction collector 9 and a microflow $F_2$ towards the micromixer 3. The split ratio achieved by the microflow splitter device according to the invention is in the range of 1000:1 to 10000:1. A split ratio of 5000:1 can be achieved with water as a solvent. The split ratio is achieved by using different tubing lengths and diameters making use of the Hagen-Poiseuille relationship:

$$F = (\pi \Delta p\ r^4)/(8L\eta) \tag{1}$$

where F is the flow rate through the tubing, $\Delta p$ is the pressure difference along the tubing, r is the radius of the tubing, L is the length of the tubing, and $\eta$ is the viscosity of the fluid passing through the tubing.

Theoretically, the split ratio is determined by the following equation:

$$\text{split ratio} = \text{flow } F_1/\text{flow } F_2$$

where flow $F_1$ is the flow rate through the tubing 8 and flow $F_2$ is the flow rate through tubing 4. $F_1$ and $F_2$ can be calculated by the same equation (1) mentioned above. Experimentally, the split ratio was determined by setting up a flow apparatus as depicted in FIG. 2. The microflow splitter 1 is placed as a connection between two closed circuits of flow 15, 16: the HPLC flow (25 ml/min) and the make-up flow (0.1–1.0 ml/min). The flows are started simultaneously and allowed to run at a constant flow rate and solvent composition (water or acetonitrile) for 24–96 hrs.

The split in the flow causes the volume in a graduated cylinder 17 to increase as a function of the split ratio and the time the experiment is run. The flow rate of the microflow is determined by measuring the change in volume in the cylinder 17 and dividing this by the time the experiment is run (flow=volume/time). The split ratio is determined as the flow rate of the HPLC flow divided by the flow rate of the microflow. This can be measured this way because the small change in the HPLC flow is negligible (i.e. <<1%). The experiment verifies the split ratio determined theoretically using the Hagen-Poiseuille equation in a range of ±10%.

Critical to the efficiency of the microsplitter device according to the invention is the proper use of the diameters for the microbore tubing 4 as well as for the tube 8 leading to the fraction collector 9. The microbore tubing 4 consists of a fused silica microbore tubing having a radius of 10–25 μm, preferably 15 μm and a length of 2–10 cm, preferably 5 cm. The tube 8 to the fraction collector 9 should consist of a wide bore tube and has typically a diameter of 40–80 Ths. (1 Th.=1/1000 inch), preferably 60 Ths. The HPLC tubing 6 consists typically of PEEK or stainless steel and has a diameter of 10–30 Ths, and a length of 5–50 cm, preferably 10–30 cm. A filter frit 18 is arranged between the port 7 and the entrance of the wide bore tubing 8 in order to ensure laminar flow. In the event that this frit 18 is absent, turbular flow could result causing sample broadening and re-mixing of the samples. Use of smaller diameters and/or longer lengths of the tubing 8 could result in severe sample broadening due to wall effects. Further, a back pressure regulator 19 is installed at the end of the wide bore tubing 8 to avoid erratic fluctuations of the flow and to obtain a controlled split ratio, since the flows $F_1$ and $F_2$ are dependent on the pressure difference $\Delta p$. Useful back pressures range from 20–100 psi, preferably 20–50 psi.

The HPLC flow is typically 10–50 ml/min. With a split ratio of 5000:1, a microflow of 2–10 μl/min is obtained. To guarantee the transport of the microflow to the detector a make-up flow of 0.1–1.5 ml/min is provided. The microflow $F_2$ is mixed with the make-up flow in the micromixer 3 and then transferred to the detector 14. In order to delay the arrival of the flow $F_1$ to the fraction collector, the time required to pass through tube 8 must be greater than that of tube 13. Preferably the length of the tubing 8 is about 90–150 cm and a delay time of about 1–7 seconds is achieved. This makes it possible to delay the sample from arriving at the fraction collector prior to detection by the mass spectrometer or other detectors.

The effects of a microflow splitter device on the peak width of a sample are demonstrated in FIG. 3 and FIG.4. The graphs in FIG. 3 and FIG. 4 are all on the same scale. The same sample flow conditions were used for all experiments in orders directly compare the peak widths of the reference sample. In FIG. 3 (A) the peak width of a reference sample without any splitter is shown. Using a commercially available splitter device on a HPLC system results in a peak broadening which is demonstrated in FIG. 3(B). As the collection of the samples takes place in a collection window which is determined by the mass spectrometer the samples denoted in gray in FIG. 3(B) are not collected by the sample collector and therefore are lost. The vertical lines denote the width of a sample that would be collected if the sample were detected by an MS detector. The effect of the microflow splitter according to the invention is demonstrated in FIG. 4(B). In comparison to the commercially available splitter, a sharper peak is achieved leading to less loss of sample. The "gray" area is smaller and the peak width (measured at half height) is very close to the peak width of the reference sample without a microflow splitter. Further, since for a split ratio of 1000:1 to 10,000:1 only a small amount of the sample is used for the detection signal, a higher resolution of the detection signal is achieved. This, together with the suppression of the broadening of the sample due to wall effects, results in a recovery rate of 85–90% of the sample delivered by the HPLC in comparison to a recovery rate of 45–55% achieved by commercially available flow splitters.

What is claimed is:

1. A process of making a microflow splitter device for the conversion of conventional flow rates (ml/min) into microflow rates (μl/min) in microseparation techniques, comprising of the following steps:

placing a micromixer (3) behind a microsplitter (2);

connecting said microsplitter (2) with said micromixer (3) by means of a microbore tubing (4);

connecting a wide bore tubing (8) for the flow towards the fraction collector (9) with the microsplitter (2);

inserting a back pressure regulator (19) into said wide bore tubing (8); and inserting a filter frit (18) into said wide bore tubing (8).

2. A process according to claim 1, wherein the microsplitter (2) consists of a T-fitting.

3. A process according to claim 1, wherein the wide bore tubing (8) has a diameter of 40–80 Ths.

4. A process according to claim 1, wherein the microbore tubing (4) is of fused silica with a radius of 10–25 μm.

5. A process according to claim 1, wherein the microbore tubing (4) has a length of 2–10 cm.

6. A process according to claim 1, wherein a filter frit (18) is placed at the entrance of the wide bore tubing (8).

7. A process according to claim 1, wherein said back pressure regulator (19) is placed at the end of the wide bore tubing (8).

8. A process according to claim 1, wherein the back pressure created by the back pressure regulator (19) is in the range from 20–100 psi.

9. A process according to claim 1, wherein the split ratio is in the range from 1000:1 to 10,000:1.

10. A microflow splitter device for the conversion of conventional flow rates (ml/min) into microflow rates (μl/min) in microseparation techniques, comprising a microsplitter (2) and a micromixer (3), which are connected by a microbore tubing (4), wherein said micromixer (3) is placed after said microsplitter (2) and wherein the microsplitter (2) is connected with a wide bore tubing (8) for the flow towards the fraction collector (9) which is equipped with a back pressure regulator (19) and a filter frit (18).

11. A microsplitter device according to claim 1, wherein the microsplitter (2) consists of a T-fitting.

12. A microsplitter device according to claim 1, wherein the micromixer (3) consists of a T-fitting.

13. A microsplitter device according to claim 1, wherein the wide bore tubing (8) has a diameter of 40–80 Ths.

14. A microsplitter device according to claim 1, wherein the microbore tubing (4) is of fused silica with a radius of 10–25 μm.

15. A microsplitter device according to claim 1, wherein the microbore tubing (4) has a length of 2–10 cm.

16. A microsplitter device according to claim 1, wherein a filter frit (18) is placed at the entrance of the wide bore tubing (8).

17. A microsplitter device according to claim 1, wherein said back pressure regulator (19) is placed at the end of the wide bore tubing (8).

18. A microsplitter device according to claim 1, wherein the back pressure created by the back pressure regulator (19) is in the range of 20–100 psi.

19. A microsplitter device according to claim 18, wherein the back pressure created by the back pressure regulator is in the range of 20–50 psi.

* * * * *

UNITED STATES PATENT AND TRADEMARK OFFICE
CERTIFICATE OF CORRECTION

PATENT NO.     : 6,289,914 B1
DATED          : September 18, 2001
INVENTOR(S)    : Ruben A. Tommasi It is certified that error appears in the above-identified patent and that said Letters Patent is hereby corrected as shown below:

Column 3,
Line 47, should read -- in order to directly compare the peak widths of the reference --

Column 4,
Line 43, should read -- A microsplitter device according to claim 10, wherein the microsplitter (2) consists of a T-fitting. --
Line 45, should read -- A microsplitter device according to claim 10, wherein the micromixer (3) consists of a T-fitting. --
Line 47, should read -- A microsplitter device according to claim 10, wherein the wide bore tubing (8) has a diameter of 40-80 Ths. --
Line 49, should read -- A microsplitter device according to claim 10, wherein the microbore tubing (4) is of fused silica with a radius of 10-25 $\mu$m. --
Line 51, should read -- A microsplitter device according to claim 10, wherein the microbore tubing (4) has a length of 2-10 cm. --
Lines 53, 56 and 59, should read -- A microsplitter device according to claim 10, wherein --

Signed and Sealed this

Twenty-ninth Day of October, 2002

*Attest:*

*Attesting Officer*

JAMES E. ROGAN
*Director of the United States Patent and Trademark Office*